US005766483A

United States Patent [19]
Luly et al.

[11] Patent Number: 5,766,483
[45] Date of Patent: Jun. 16, 1998

[54] PROCESS FOR HYDROGEN FLUORIDE SEPARATION

[75] Inventors: Mathew Hermes Luly, Lancaster; Jeffrey Warren Mckown, East Aurora, both of N.Y.; Robert Pratt, Randolph, N.J.; Rajiv Ratna Singh, Getzville, N.Y.; Paul Frederick Kunkel, Cheektowaga, N.Y.; Charles Lewis Redmon, Orchard Park, N.Y.; Hang Thanh Pham, Amherst, N.Y.

[73] Assignee: AlliedSignal Inc., Morristown, N.J.

[21] Appl. No.: 644,546

[22] Filed: May 10, 1996

[51] Int. Cl.$^6$ .................... B01D 53/14; B01D 15/00
[52] U.S. Cl. ............... 210/670; 423/484; 423/240 R; 95/131
[58] Field of Search .................. 423/483, 484, 423/240 R, 488, 648.1; 95/131; 210/670, 679

[56] References Cited

U.S. PATENT DOCUMENTS

| | | | |
|---|---|---|---|
| 3,140,916 | 7/1964 | Lowdermilk | 23/154 |
| 3,314,755 | 4/1967 | Claus | 423/483 |
| 3,553,938 | 1/1971 | Hirayama et al. | 55/71 |
| 3,616,611 | 11/1971 | Gentili | 423/489 |
| 3,773,907 | 11/1973 | Blochl et al. | 423/484 |
| 3,798,875 | 3/1974 | Morris | 423/483 |
| 3,947,558 | 3/1976 | van Eijl | 423/481 |
| 4,157,376 | 6/1979 | Vulikh et al. | 423/488 |
| 4,209,470 | 6/1980 | Lorquet | 260/652 |
| 4,383,868 | 5/1983 | Braley | 210/678 |
| 4,629,610 | 12/1986 | Friese et al. | 423/240 R |
| 4,640,831 | 2/1987 | DeVries | 423/481 |
| 4,882,134 | 11/1989 | Mizrahi | 423/356 |
| 4,902,312 | 2/1990 | Chang | 55/71 |
| 4,943,360 | 7/1990 | Sugisawa et al. | 204/182.3 |
| 4,985,220 | 1/1991 | Andeh et al. | 423/483 |
| 4,999,095 | 3/1991 | Chlanda et al. | 204/182.4 |
| 5,032,371 | 7/1991 | Buehler | 423/484 |
| 5,139,632 | 8/1992 | Chlanda et al. | 204/182.4 |
| 5,196,616 | 3/1993 | Lee et al. | 570/178 |
| 5,211,020 | 5/1993 | Taylor et al. | 62/11 |
| 5,211,817 | 5/1993 | Adams et al. | 203/82 |
| 5,298,229 | 3/1994 | Hardwick | 423/240 S |
| 5,458,674 | 10/1995 | Barsotti | 92/122 |

FOREIGN PATENT DOCUMENTS

| 665932 | 6/1979 | U.S.S.R. | 95/131 |
|---|---|---|---|
| WO 9420412 | 9/1994 | WIPO . | |
| WO 95/16740 | 6/1995 | WIPO . | |

OTHER PUBLICATIONS

Chemical Abstract : 112 : 124378e, "Study of Products . . . fibrous sorbent", Asaulova et al, Apr. 1990.
Chemical Abstract: 95:52004q, "Selection of effective . . . gas–air medium", Komarov et al, 2, 1981.

*Primary Examiner*—Ngoc-Yen Nguyen
*Attorney, Agent, or Firm*—Colleen D. Szuch; Jay P. Friedenson

[57] ABSTRACT

A method for separating hydrogen fluoride from a chemical mixture is provided. In the process of the invention, hydrogen fluoride is separated from a chemical mixture containing hydrogen fluoride by contacting the chemical mixture with a hydrogen fluoride binder. The separated hydrogen fluoride may be recovered from the hydrogen fluoride binder.

28 Claims, No Drawings

PROCESS FOR HYDROGEN FLUORIDE SEPARATION

FIELD OF THE INVENTION

The present invention relates to a method for separating hydrogen fluoride from a chemical mixture. More specifically, a method is provided for separating hydrogen fluoride from a chemical mixture containing hydrogen fluoride by contacting the chemical mixture with a hydrogen fluoride binder.

BACKGROUND OF THE INVENTION

Hydrogen fluoride is widely used in industry for a variety of processes including in fluorocarbon and fluoropolymer manufacture, in alkylation reactions, and in fluorine manufacture. In these processes, it is desirable to separate the hydrogen fluoride from the other reactants, products, and impurities. However, hydrogen fluoride can be difficult to separate. This is especially true in fluorocarbon manufacture because hydrogen fluoride forms an azeotropic mixture with many fluorocarbons.

A number of methods have been developed in order to separate hydrogen fluoride from chemical mixtures. The known methods include the use of sodium fluoride, alkaline earth compounds, carbon molecular sieves, water-immisicible amines, oleum, distillation, membranes, and electrodialysis to facilitate separation of the hydrogen fluoride. Each of the known methods is disadvantageous in that these processes are inefficient, uneconomical, or produce a toxic waste stream.

Additionally, U.S. Pat. No. 5,458,674 discloses a process for separating hydrogen fluoride from a mixture of hydrocarbons and hydrogen fluoride by adsorbing or absorbing hydrogen fluoride onto a fluorinated polymer. This process is disadvantageous in that only 10 to 15 weight percent of hydrogen fluoride based on the weight of the polymer can be adsorbed or absorbed before the polymer must be regenerated.

U.S. Pat. No. 4,640,831 discloses a process for recovering protic acids, including hydrofluoric acid, from a medium. The process uses a reversible base that is an aromatic compound with one or more nitrogen atoms in an aromatic ring or a polymer with pendant aromatic compounds with one or more nitrogen atoms in an aromatic ring. The disclosed process is disadvantageous in that high temperatures are required for recovery of the hydrogen fluoride.

Therefore, a need exists for a hydrogen fluoride separation method that attempts to overcome the disadvantages of the prior art methods.

DESCRIPTION OF THE INVENTION AND PREFERRED EMBODIMENTS

This invention provides a continuous, intermittent, or batch process for separating hydrogen fluoride from a hydrogen fluoride-containing chemical mixture. The process of the invention provides a convenient and cost-effective method for separating hydrogen fluoride.

The process of the invention comprises contacting a first chemical mixture containing hydrogen fluoride with a hydrogen fluoride binder under conditions suitable to separate hydrogen fluoride from the mixture to produce a second chemical mixture in which the amount of hydrogen fluoride is reduced. The process may also provide for recovering the hydrogen fluoride from the binder for reuse and regeneration of the binder.

It is to be understood that separating includes both isolating hydrogen fluoride from a mixture as well as purifying the hydrogen fluoride by removing impurities from the hydrogen fluoride. Further, for purposes of this invention, a chemical mixture is a liquid or vapor phase mixture of inorganic material, organic material, or mixtures thereof. Illustrative inorganic materials include, without limitation, hydrogen, hydrogen chloride, sulfur dioxide, sulfur trioxide, carbon monoxide, carbon dioxide, boron trifluoride, uranium hexafluoride, sulfur hexafluoride, arsenic pentafluoride, halide salts, nitric acid, sulfuric acid, chlorine, metal ions, non-aqueous inorganic solvents, and mixtures thereof. Exemplary organic material includes, without limitation, halocarbons such as chlorofluorocarbons, hydrochlorofluorocarbons, hydrofluorocarbon, and perfluorocarbons, chlorocarbons, hydrochlorocarbons, hydrofluoroethers, fluoroethers, hydrocarbons, and mixtures thereof.

The process of the invention may be carried out in any suitable corrosion resistant vessel. In the process of the invention, a first chemical mixture containing hydrogen fluoride is contacted with a hydrogen fluoride binder for at least about 0.1 seconds, more preferably from about 0.1 to about 100,000 seconds, still more preferably from about 1 to about 10,000 seconds, and most preferably from about 2 to about 100 seconds. The hydrogen fluoride binder of the invention may be any polymer capable of reversibly binding hydrogen fluoride. Preferably the polymer is inert, or substantially inert, to hydrogen fluoride. For purposes of this invention, polymer may be a homopolymer, copolymer, or mixtures thereof.

Generally, the polymers used in the invention have molecular weights of from about 5,000 to about 10,000,000. Preferably, polymers with molecular weights of from about 5,000 to about 1,000,000 are used. The polymers useful as binders in the invention are water-soluble polymers. By "water-soluble polymer" is meant any high molecular weight compound that swells, to about twice its dry volume, or dissolves with the addition of water at room temperature.

Water-soluble polymer is meant to include semi-synthetic water-soluble polymers, synthetic water-soluble polymers, and mixtures thereof. Semi-synthetic water-soluble polymers are natural water-soluble polymer derivatives. Synthetic water-soluble polymers are not natural water-soluble polymer derivatives and are formed only through chemical reactions.

Exemplary semi-synthetic water-soluble polymers include, without limitation, cellulose ethers, modified starches, starch derivatives, natural gum derivatives, and mixtures thereof. Illustrative synthetic water-soluble polymers include, without limitation, polymers, related polymers, and polymer salts of acrylamide, acrylic acid, ethylene oxide, methacrylic acid, polyethyleneirnine, polyvinyl alcohol, polyvinyl pyrrolidone, and mixtures thereof. By related polymer is meant that the polymer repeat unit, or a branch thereof, is extended by carbon atoms, preferably from one to four carbon atoms. For example, a related polymer of acrylic acid is one in which the vinyl group is extended by one carbon to form an allyl group.

Preferably, a synthetic water-soluble polymer is used. More preferably, polyacrylic acid or one of its salts is used. Most preferably, the water-soluble polymer is sodium polyacrylate.

The polymer may be selected in order to separate hydrogen fluoride alone. Alternatively, it may be selected so as to separate hydrogen fluoride and any other material from the chemical mixture.

The form of the binder, such as liquid or solid, may be tailored for use with the process that produces the chemical mixture. The amount of binder used will depend on the specifics of the process producing the chemical mixture. Such specifics include, without limitation, the quantity of hydrogen fluoride to be separated from the first chemical mixture, the desired frequency of binder regeneration, the acceptable content of hydrogen fluoride in the second chemical mixture, the flow rate of the first chemical mixture, and the absorption characteristics of the polymer. Generally, the amount of binder used will be an amount effective to separate the desired amount of hydrogen fluoride from the first chemical mixture.

In one embodiment of the invention, the binder is in the form of particles, fibers, or a shaped piece or pieces and the binder is placed in a vessel to form a packed bed of binder. The first chemical mixture is contacted with the binder by passing the mixture through the column in order to separate hydrogen fluoride from the mixture to produce a second chemical mixture that has a reduced hydrogen fluoride content. Generally, contacting may be performed at the temperature at which the first chemical mixture was formed. More particularly, contacting is performed at temperatures less than about 200° C., preferably at less than about 150° C., more preferably at less than about 120° C., and most preferably at less than about 100° C. Contacting may be performed at any pressure, but preferably is performed at atmospheric or superatmospheric pressure.

The performance of the binder may be improved by periodically regenerating the binder to release the hydrogen fluoride separated from the first chemical mixture. Regeneration may be accomplished by subjecting the binder to a reduced pressure, including a vacuum, to release hydrogen fluoride vapor which may be then recovered by any convenient means such as a cold trap. Alternatively, the binder may be subjected to a vacuum and temperatures from about 0° C. to about 200° C., preferably from about 80° C. to about 125° C., to speed the release of hydrogen fluoride vapor. As yet another alternative, the binder may be heated in the presence of a gas or solvent capable of carrying the hydrogen fluoride to another part of the process. The gases useful in this embodiment are any gases that are inert to the hydrogen fluoride and polymer including, without limitation, air, nitrogen, helium, and argon. In cases in which the binder is being used as a part of a chemical process the hydrogen fluoride and gas may be returned to the process or the hydrogen fluoride vapor isolated.

The amount of hydrogen fluoride bound to the binder must be controlled in order to maintain the mechanical integrity of the binder. If the binder is in solid form, allowing the amount of hydrogen fluoride separated from the first chemical mixture and bound by the binder to reach a level at which the binder turns from a solid into a gel or liquid may be disadvantageous. The amount of hydrogen fluoride at which this phase change occurs will vary depending on the binder used. Generally, when the separated hydrogen fluoride makes up about 80 weight percent, based on the combined weight of the binder and the separated hydrogen fluoride, the binder will be a viscous liquid. Binders with less than about 80 weight percent hydrogen fluoride will be gel-like solids. Preferably, binding of hydrogen fluoride is carried out up to the amount at which a phase change occurs. Hydrogen fluoride separation and binding may be monitored by any convenient means as for example, measuring the amount of hydrogen fluoride in the chemical mixtures or maintaining the temperature of the binder bed at a point at which the polymer cannot bind sufficient hydrogen fluoride to undergo a phase change. Further, if one or more other chemicals in the first chemical mixture forms a gel or solid with the binder, the hydrogen fluoride absorption required for the solid to liquid phase change may be altered.

The process of the invention may include recovering the separated hydrogen fluoride from the binder. The hydrogen fluoride may be recovered from the binder by first applying heat, applying a vacuum, using a stripping gas or solvent, or any combination thereof. The hydrogen fluoride removed from the binder by the heating or vacuum is then condensed by cooling. Generally, the higher the temperature, the higher is the vapor pressure of hydrogen fluoride above the binder vapor pressure and the less vacuum and cooling will be required to condense the hydrogen fluoride. Temperatures are determinable by one ordinarily skilled in the art by a consideration of the binder used. Generally, temperatures from about 0° C. to about 200° C., preferably from about 80° C. to about 125° C., are used.

If the process of the invention is used in a continuous mode and it is desirable to recover the hydrogen fluoride from the binder, preferably, at least two binder beds are employed in order to provide that at least one binder bed is continuously available while hydrogen fluoride is being recovered from the other bed. Additionally, if very low levels of hydrogen fluoride are desired in the second chemical mixture, that mixture may be treated sequentially with more than one binder bed to reach the desired hydrogen fluoride level. Alternatively, the process of the invention may be used in conjunction with one of the well known hydrogen fluoride separation methods.

The invention will be clarified further by a consideration of the following examples that are purely exemplary.

EXAMPLES

Example 1

7.0 g of sodium polyacrylate, m wt 1,000,000, were placed in a PFA cylinder, the cylinder evacuated and 27.6 g HF added. The cylinder was shaken for 1 hour. All of the HF was absorbed by the sodium polyacrylate. The PFA cylinder was then heated to 105° C. to drive off the HF, which was recovered in an attached Monel cylinder cooled in a liquid nitrogen bath. 25.4 g HF were recovered.

Example 2

Cylinder A, a 150 cc Monel cylinder, was charged with 4.0 g sodium polyacrylate, m wt 1,000,000, and evacuated. A mixture of 4.0 g HF and 75.7 g chlorodifluoromethane, HCFC-22, was distilled into cylinder A. Cylinder A and its contents were then placed on a mechanical shaker for 30 minutes and, subsequently, vented into an evacuated 1,000 cc ice-cooled cylinder, cylinder B. During the venting step, cylinder A lost 72.7 g of material to cylinder B. The contents of cylinder B were mixed with water and titrated. Cylinder B contained 0.26 g HF and 72.44 g HCFC-22. Cylinder A was then heated at about 100° C. and 5.6 g material were evolved. The material was collected and analyzed and found to be 2.76 g HF and 2.76 g HCFC-22. A gas chromatogram of the collected HCFC-22 was identical to that of the starting material indicating that no decomposition occurred.

Example 2 demonstrates that sodium polyacrylate preferentially mixes with HF rather than HCFC-22 and, thus, contacting a mixture of HF and HCFC-22 with sodium polyacrylate separates hydrogen fluoride from the mixture.

Example 3

The procedure of Example 2 was used except that 5.0 g sodium polyacrylate, m wt 1,000,000, 78.2 g CFC-12 and 5.0 g HF were substituted for the sodium polyacrylate, HCFC-22 and HF, respectively, of Example 2. Cylinder A, when vented, lost 75.7 g that was analyzed and found to be 0.75 g HF, 74.98 g CFC-12. Upon heating cylinder A to approximately 100° C., 3.8 g HF and 2.4 g CFC-12 were recovered.

Example 4

A mixture of 26.6 g 1,1,1,3,3-pentachloropropane, HCC-240, and 1.6 g HF was added to a PFA cylinder containing 1.8 g sodium polyacrylate, m wt 1,000,000. The mixture was shaken for 1 hour and 22.1 g of liquid decanted from the resulting gel-like solid. The liquid was washed with water, phase separated and analyzed which demonstrated that it contained 0.01 g HF and 22.0 g organic. Heating the get-like solid at approximately 100° C. for 1 hour released 2.1 g of material that was collected in an evacuated cylinder and analyzed as 1.06 g HF and 1.04 g organic.

Example 5

The procedure of Example 4 was used except that 1.6 g sodium polyacrylate, m wt 1,000,000, 24.8 g HCFC-141b, and 1.3 g HF were substituted for the sodium polyacrylate, HCC-240 and HF of Example 4. 21.5 g of liquid were decanted from the gel-like solid. The liquid was analyzed and found to be 0.01 g HF and 21.4 g organic. Heating the gel-like solid at 100° C. drove 3.8 g of material from the gel that was analyzed and found to be 0.33 g HF and 3.47 g HCFC-141b.

Example 6

The procedure of Example 4 was used except that 1.5 g sodium polyacrylate, m wt 1,000,000, 25.6 g $C_2Cl_4$ and 1.3 g HF were substituted for the sodium polyacrylate, CC-240 and HF of Example 4. 21.0 g of liquid were decanted from the gel that was analyzed and found to be 0.004 g HF and 21 g $C_2Cl_4$. Heating of the gel at 100° C. recovered an additional 3.6 g of material that was determined to be 0.52 g HF and 3.08 g organic.

Example 7

The procedure of Example 2 was used except that 1.1 g sodium polyacrylate, m wt 1,000,000, 22.4 g isobutane and 1.0 g HF were substituted for the sodium polyacrylate, HCFC-22 and HF of Example 2. 22.1 g of material was not absorbed by the polymer and was vented after the 1 hour of shaking. This material was analyzed and found to be 0.07 g HF and 22.03 g organic. Heating the remaining material at approximately 100° C. for 1 hour released 1.1 g of material that was analyzed and found to be 0.47 g HF and 0.63 g organic.

Example 8

The procedure of Example 2 was used except that 1.7 g sodium polyacrylate, m wt 1,000,000, 16.8 g octafluoropropane, FC-218, and 1.7 g HF were substituted for the sodium polyacrylate, HCFC-22 and HF of Example 2. 15.6 g of material was not absorbed by the polymer after shaking and was vented from the cylinder. This vented material was analyzed as 0.03 g HF and 15.57 g organic. Heating of the material in Cylinder A at approximately 100° C. for 1 hour released 2.2 g of material that was analyzed and found to be 0.81 g HF and 1.4 g organic.

Example 9

The procedure of Example 2 was used except that 7.5 g sodium polyacrylate, m wt 1,000,000, 20.0 g 1,1,1,3,3-pentafluoropropane, HFC-245fa, and 6.5 g HF were substituted for the sodium polyacrylate, HCFC-22 and HF of Example 2. After shaking the mixture, the cylinder was vented and lost 20.0 g of material that was analyzed and found to be 0.5 g HF and 19.5 g HFC-245fa.

Example 10

The procedure of Example 4 was used except that 1.6 g sodium polyacrylate, m wt 1,000,000, 19.4 g tetrahydrofuran and 1.7 g HF were substituted for the sodium polyacrylate, CC-240 and HF of Example 4. 18.5 g of material did not form a gel after 1 hour of shaking and was decanted from the vessel. This liquid was analyzed and found to be about 1.4 g HF. An additional 1.2 g material were released when the gel was heated at approximately 100° C. for 1 hour and found to be mainly tetrahydrofuran.

Example 11

The procedure of Example 2 was followed except that 1.62 g sodium polyacrylate, m wt 1,000,000, 0.1 g $H_2$ and 1.66 g HF were substituted for the sodium polyacrylate, HCFC-22 and HF of Example 2. After 1 hour of shaking, the cylinder was vented and 0.1 g of material was lost. The vented material contained 0.015 g HF. Heating the cylinder at approximately 100° C. for 2.5 hours released 0.3 g of material that contained 0.17 g HF.

Example 12

30.0 g of sodium polyacrylate, m wt 1,000,000, were placed in a vessel and 50.0 g of a 1 weight percent HF/99 weight percent HCl mixture were passed over the sodium polyacrylate in a 15 minute period. The collected gas had 3 to 5 times less HF than the starting mixture.

Example 13

The procedure of Example 2 was followed except that a mixture of 27.5 g HCFC-22, 21.0 g HCl, and 1.5 g HF was distilled into a cylinder charged with 1.5 g sodium polyacrylate, m wt 1,000,000. After shaking the mixture for 1 hour, the cylinder was vented and lost 46.1 g that was analyzed and found to be 26.6 g HCFC-22, 0.3 g HF and 22.5 G HCl. Heating the remaining gel at approximately 100° C. for 2 hours liberated 0.9 g HF, 1.2 g HCl and 0.1 g HCFC-22.

Example 14

The procedure in Example 2 was followed except that 1.6 g sodium polyacrylate, m wt 1,00,000, 20.4 g HCFC-22, 1.5 g HF and 21.3 g $CO_2$ were substituted for the sodium polyacrylate, HCFC-22 and HF, respectively, of Example 2. After shaking the mixture for 1 hour, the cylinder was vented and lost 41.4 g of material containing 0.18 g HF. Heating of the gel at approximately 100° C. released 1.7 g of material that contained 1.0 g HF.

Example 15

The procedure of Example 6 was used except that 1.5 g poly(acrylic acid-co-maleic acid)sodium salt, m wt 50,000, 1.8 g HF and 25.0 g $C_2Cl_4$ were used. After 1 hour, 18.2 g of liquid were decanted and found to be 0.002 g HF and 18.2 g $C_2Cl_4$. Heating of the gel at approximately 90° C. for 1 hour drove off about 1.8 g of material, most of which was HF.

Example 16

The procedure in Example 2 was followed except that 1.8 g NAFION™ NR50, 1.7 g HF and 22.9 g HCFC-22 were used. After 1 hour, 24 g of material were not absorbed on the polymer (0.7 g HF and 23.3 g HCFC-22). Heating the polymer at 90° C. for 1 hour yielded 0.8 g of material that analyzed as 0.6 g HF and 0.2 g HCFC-22.

Example 16 demonstrates that the NAFION™ polymer has a lower capacity for separating hydrogen fluoride from a chemical mixture than the binder of Example 2.

Example 17

The procedure of Example 2 is used except that 7.0 g acrylic acid, m wt 1,250,000, are substituted for the sodium polyacrylate of Example 2. When cylinder A is vented to cylinder B, all of the HCFC-22 and only a trace of HF are measured in cylinder B. Heating cylinder A liberates essentially all 4.0 g of HF used in the experiment demonstrating the separation of HF and HCFC-22 with polyacrylic acid.

Example 18

The procedure of Example 2 is used except that 7.0 g polyacrylate copolymerized with 20 wt percent, 50,000 m wt acrylamide are substituted for the sodium polyacrylate of Example 2. When cylinder A is vented to cylinder B, all of the HCFC-22 and only a trace of HF are measured in cylinder B. Heating cylinder A liberates essentially all 4.0 g of HF used in the experiment demonstrating the separation of HF and HCFC-22.

Example 19

The procedure of Example 2 is used except that 7.0 g acrylic acid copolymerized with 10 wt percent, 200,000 m wt acrylamide are substituted for the sodium polyacrylate of Example 2. When cylinder A is vented to cylinder B, all of the HCFC-22 and only a trace of HF are measured in cylinder B. Heating cylinder A liberates essentially all 4.0 g of HF used in the experiment demonstrating the separation of HF and HCFC-22.

Example 20

The procedure of Example 2 is used except that 7.0 g of 2,100 m wt sodium polyacrylate are substituted for the sodium polyacrylate of Example 2. When cylinder A is vented to cylinder B, all of the HCFC-22 and only a trace of the HF are measured in cylinder B. Heating liberates essentially all 4.0 g of HF used in the experiment.

Example 21

The procedure of Example 2 is used except that 7.0 g sodium polyacrylate copolymerized with 10 wt percent, 15,000 m wt methylmethacrylate are substituted for the sodium polyacrylate of Example 2. When cylinder A is vented to cylinder B, all of the HCFC-22 and only a trace of the HF are measured in cylinder B. Heating cylinder liberates essentially all 4.0 g of HF used in the experiment demonstrating the separation of HF and HCFC-22 with this polymer.

Example 22

The procedure of Example 2 is used except that 7.0 g polyethylene oxide, m wt 10,000,000 are substituted for the sodium polyacrylate of Example 2. When cylinder A is vented to cylinder B, all of the HCFC-22 and only a trace of H are measured in cylinder B. Heating cylinder A liberates essentially all 4.0 g of the HF used in the experiment demonstrating the separation of HF and HCFC-22.

Example 23

The procedure of Example 2 is used except that 7.0 g polymethacrytic acid, m wt 2,500,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

Example 24

The procedure of Example 2 is used except that 7.0 g polymethacrylamide, m wt 250,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

Example 25

The procedure of Example 2 is used except that 7.0 g polyvinyl alcohol, m wt 500,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

Example 26

The procedure of Example 2 is used except that 7.0 g polyvinyl pyrrolidone, m wt 50,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

Example 27

The procedure of Example 2 is used except that 7.0 g polyethyleneimine, m wt 750,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

Example 28

The procedure of Example 2 is used except that 7.0 g polyacrylamide, m wt 100,000 are substituted for the sodium polyacrylate of Example 2. When cylinder A is vented to cylinder B, all of the HCFC-22 and only a trace of the HF are measured in cylinder B. Heating cylinder A liberates essentially all 4.0 g HF used in the experiment.

What is claimed is:

1. A process for separating hydrogen fluoride from a chemical mixture comprising contacting a first chemical mixture containing hydrogen fluoride with a hydrogen fluoride binder to separate hydrogen fluoride from the first chemical mixture to form a second mixture with a reduced content of hydrogen fluoride wherein the hydrogen fluoride binder is a synthetic water soluble acrylic acid polymer.

2. The process of claim 1 wherein the acrylic acid polymer is a polyacrylic acid salt.

3. The process of claim 2 wherein the polyacrylic acid salt is sodium polyacrylate.

4. The process of claim 1 wherein the acrylic acid polymer has a molecular weight of from about 5,000 to about 1,000,000.

5. The process of claim 3 wherein the sodium polyacrylate has a molecular weight of from about 5,000 to about 1,000,000.

6. The process of claims 2 or 3 wherein contacting is performed at temperatures less than about 150° C.

7. The process of claim 6 wherein the contacting is performed at temperatures less than about 120° C.

8. The process of claim 6 wherein contacting is performed at temperatures less than about 100° C.

9. The process of claim 1 further comprising the step of regenerating the hydrogen fluoride binder at a temperature of from about 80° C. to about 125° C. to release separated hydrogen fluoride.

10. The process of claim 1 further comprising the step of recovering the separated hydrogen fluoride from the binder at a temperature of from about 80° C. to about 125° C.

11. The process of claims 1, 2 or 3 wherein the chemical mixture is a vapor phase mixture.

12. The process of claims 1, 2 or 3 wherein the chemical mixture is a liquid phase mixture.

13. The process of claim 11 wherein the vapor phase mixture is a mixture of inorganic material.

14. The process of claim 13 wherein the inorganic material is hydrogen.

15. The process of claim 13 wherein the inorganic material is hydrogen chloride.

16. The process of claim 11 wherein the vapor phase mixture is a mixture of organic material.

17. The process of claim 16 wherein the organic material is hydrofluorocarbons, hydrochlorofluorocarbons, perfluorocarbons, chlorofluorocarbons, or mixtures thereof.

18. The process of claim 12 wherein the liquid phase mixture is a mixture of organic material.

19. The process of claim 18 wherein the organic material is hydrofluorocarbons, hydrochlorofluorocarbons, perfluorocarbons, chlorofluorocarbons, or mixtures thereof.

20. The process of claim 11 wherein contacting is performed at less than about 150° C.

21. The process of claim 11 wherein contacting is performed at less than about 120° C.

22. The process of claim 11 wherein contacting is performed at less than about 100° C.

23. The process of claim 17 wherein contacting is performed at less than about 150° C.

24. The process of claim 17 wherein contacting is performed at less than about 120° C.

25. The process of claim 17 wherein contacting is performed at less than about 100° C.

26. The process of claim 19 wherein contacting is performed at less than about 150° C.

27. The process of claim 19 wherein contacting is performed at less than about 120° C.

28. The process of claim 19 wherein contacting is performed at less than about 100° C.

* * * * *

UNITED STATES PATENT AND TRADEMARK OFFICE
CERTIFICATE OF CORRECTION

PATENT NO. : 5,766,483
DATED : June 16, 1998
INVENTOR(S) : Luly et al.

It is certified that error appears in the above-identified patent and that said Letters Patent is hereby corrected as shown below:

Column 2, line 53, delete "polyethyleneimine" and substitute -- polyethyleneimine -- therefor.

Column 5, line 14, "get-like" should read -- gel-like --.

Column 6, line 24, "HCI" should read -- HCl --.

Column 6, line 35, "HCI" should read -- HCl --.

Column 7, line 48, delete "H" and substitute -- HF -- therefor.

Column 7, line 52, delete "polymethacrytic" and substitute -- polymethyacrylic -- therefor.

Signed and Sealed this

Twenty-ninth Day of February, 2000

*Attest:*

Q. TODD DICKINSON

*Attesting Officer*   *Commissioner of Patents and Trademarks*